United States Patent [19]

Lee et al.

[11] Patent Number: 4,619,917

[45] Date of Patent: Oct. 28, 1986

[54] SUBSTITUTED 2-FURANYL- OR 5-OXO-2-FURANYL METHOXY PHOSPHORYL ALKYL CYCLIMMONIUM SALTS

[75] Inventors: Mark L. Lee, Lake Hopatcong; Christian Jaeggi, Randolph, both of N.J.

[73] Assignee: Sandoz Pharm. Corp., E. Hanover, N.J.

[21] Appl. No.: 793,367

[22] Filed: Oct. 31, 1985

Related U.S. Application Data

[63] Continuation-in-part of Ser. No. 756,368, Jul. 18, 1985, abandoned, which is a continuation-in-part of Ser. No. 659,249, Oct. 10, 1984, abandoned.

[51] Int. Cl.$^4$ ................. A61K 31/665; A61K 31/675; C07F 9/58; C07F 9/65
[52] U.S. Cl. ........................................ 514/77; 514/82; 514/85; 514/89; 514/92; 546/22; 546/23
[58] Field of Search ..................... 548/112; 546/22, 23; 514/77, 82, 85, 89, 92

[56] References Cited

U.S. PATENT DOCUMENTS 4,329,302  5/1982  Hanahan et al. .................... 260/925
4,426,525  1/1984  Hozumi et al. ................. 260/925 X
4,444,766  4/1984  Bosies et al. .................... 260/925 X Primary Examiner—Richard L. Raymond
Attorney, Agent, or Firm—Gerald D. Sharkin; Robert S. Honor; Joseph J. Borovian

[57] ABSTRACT

The invention discloses certain substituted 2-furanyl- or 5-oxo-2-furanyl methoxy phosphoryl alkyl cyclimmonium salts useful as PAF inhibitors, pharmaceutical compositions containing said compounds as an active ingredient thereof and a method of using such compositions for inhibiting PAF-induced blood platelet aggregation, PAF-mediated bronchoconstriction and extravasation, PAF-induced hypotension and PAF-induced ischemic bowel disease.

24 Claims, No Drawings

SUBSTITUTED 2-FURANYL- OR 5-OXO-2-FURANYL METHOXY PHOSPHORYL ALKYL CYCLIMMONIUM SALTS

This application is a continuation-in-part of U.S. Patent Application Ser. No. 756,368, filed July 18, 1985, which in turn is a continuation-in-part of U.S. Patent Application Ser. No. 659,249, filed Oct. 10, 1984, both now abandoned.

The present invention relates to certain substituted 2-furanyl- or 5-oxo-2-furanyl methoxy phosphoryl alkyl cyclimmonium salts and to their use as platelet activating factor (PAF) receptor antagonists and as inhibitors of PAF-induced blood platelet aggregation. The invention also relates to pharmaceutical compositions containing the afore-mentioned compounds as an active ingredient thereof and the method of using such compositions for inhibiting PAF-mediated bronchoconstriction and extravasation, PAF-indeuced hypotension and PAF-involved ischemic bowel disease.

Blood platelets, also called thrombocytes, are well recognized as important cellular elements that circulate in the blood. Their role is to staunch bleeding by forming clots in broken blood vessels, i.e., they are nature's corks. They have, however, been implicated in a variety of immunologically mediated forms of tissue injury. Their participation in these processes involved the release of platelet activating factor (PAF) which in turn interacts with the platelets, inducing aggregation and secretion of granular constituents. As a further consequence of platelet activation, there may result a fatal reaction consisting of acute pulmonary hypertension, right heart dilation, systemic hypotension, significant increases in pulmonary vascular resistance, decrease in dynamic lung compliance and often complete pulmonary apnea. More recently, evidence has been obtained which appears to implicate platelet activating factor in the formation of fibromuscular lesions of the arterial walls of the aorta and coronary arteries, thereby contributing to the development of atherosclerosis. Further, the possible role of PAF in ischemic bowel disease, particularly necrotizing enterocolitis (NEC) has recently been described, thereby implicating PAF in the development of disorders leading to bowel necrosis.

The existence of platelet activating factor was proposed in an article by Henson, P. M., Journal of Experimental Medicine 131, 287 (1970). However, due to the limited quantities of material available for study, great difficulty was encountered in defining the chemical structure and biochemical activity of PAF.

One of the earlier reports on the chemical nature of PAF was that of Benveniste, J., Nature 249, 581 (1974), wherein the physiochemical characteristics of PAF were reported. A later study by Benveniste, J., et al., Nature 269, 170 (1977) reported on the purification of PAF isolated by successive thin layer chromatography. A more recent study by Hanahan, et al. in the J. of Biol. Chem. 225: 5514–5516 (June 1980) confirmed that the compounds, 1-O-alkyl-2-acetyl-sn-glyceryl-3-phosphorylcholine (AGEPC), and PAF are one and the same composition. Since that time, many research endeavors have been directed to the synthesis of compounds structurally related to that of PAF in an effort to uncover compounds useful in the inhibition of platelet activating factor.

The essence of the present invention is the discovery that certain substituted 2-furanyl- or 5-oxo-2-furanyl methoxy phosphoryl alkyl cyclimmonium salts of formula I:

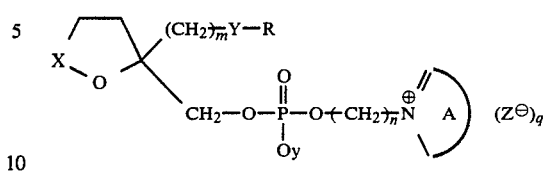

where
R is n-$C_{12}$-$C_{20}$ alkyl, alkenyl or alkynyl; or $C_{12}$-$C_{24}$ alkoxyalkyl;
X is $CH_2$ or C=O;
Y is $CH_2$; O;

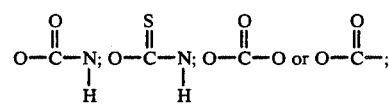

A, together with the nitrogen atom, forms an unsubstituted 5- or 6-membered, monocyclic ring which may optionally contain one further hetero atom selected from nitrogen and sulfur; a 5- or 6-membered, monocyclic ring which may optionally contain one further hetero atom selected from nitrogen and sulfur and which is either mono-, di- or trisubstituted by $C_1$-$C_4$ alkyl or monosubstituted by $CF_3$, halo, COOH or $COOCH_3$; an unsubstituted 10-membered, bicyclic ring which may optionally contain one further nitrogen atom; or a 10-membered, bicyclic ring which may optionally contain one further nitrogen atom and which is either mono-, di- or trisubstituted by $C_1$-$C_4$ alkyl or monosubstituted by $CF_3$, halo, COOH or $COOCH_3$;
$Z^\ominus$ is a pharmaceutically acceptable anion;
m is an integer 1 or 2;
n is an integer 2 to 8; and
y is $\ominus$ and q is 0 or y is H and
q is 1;
are useful as PAF receptor antagonists and as inhibitors of PAF-induced blood platelet aggregation.

Included among the compounds of formula I are the compounds of subclass Ia:

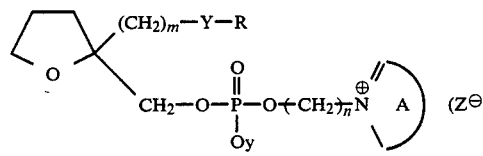

where
R, Y, A, $Z^\ominus$, m, n, y and q are as defined above.
The preferred compounds of subclass Ia are compounds of formula Ia':

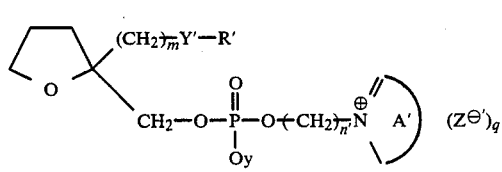

where

R' is n-$C_{14}$-$C_{20}$ alkyl, alkenyl or alkynyl; or $C_{12}$-$C_{20}$ alkoxyalkyl;

Y' is $CH_2$; O;

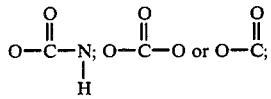

A', together with the nitrogen atom, forms an unsubstituted thiazolium, pyridinium, pyridazinium, quinolinium or isoquinolinium ring, or a thiazolium, pyridinium, pyridazinium, quinolinium or isoquinolinium ring which is either mono-, di- or trisubstituted by $C_1$-$C_4$-alkyl or monosubstituted by $CF_3$, halo, COOH or $COOCH_3$;

$Z^{\ominus'}$ is chloride; bromide; iodide; phenylsulfonate; toluenesulfonate; $C_1$-$C_4$-alkylsulfonate; carboxylate or tetrafluoroborate;

n' is an integer 2 to 6;

and m, y and q are as defined above.

The more preferred compounds of subclass Ia are compounds of formula Ia'':

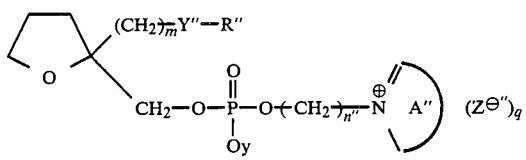

where

R'' is n-$C_{16}$-$C_{20}$ alkyl, alkenyl or alkynyl; or $C_{14}$-$C_{18}$ alkoxyalkyl;

Y'' is O;

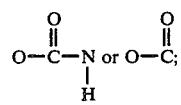

A'', together with the nitrogen atom, forms an unsubstituted thiazolium, pyridinium or quinolinium ring, or a thiazolium, pyridinium or quinolinium ring which is either mono-, di- or trisubstituted by $C_1$-$C_4$ alkyl or monosubstituted by $CF_3$, halo, COOH or $COOCH_3$;

$Z^{\ominus''}$ is chloride; bromide; $C_1$-$C_4$ alkylsulfonate or carboxylate;

n'' is an integer 2 to 4;

and m, y and q are as defined above.

The even more preferred compounds of subclass Ia are compounds of formula Ia''':

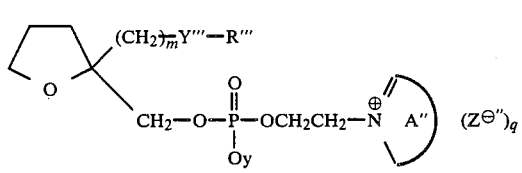

where

R''' is n-$C_{16}$-$C_{18}$ alkyl, alkenyl or alkynyl; or $C_{14}$-$C_{18}$-alkoxyalkyl;

Y''' is O;

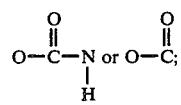

and A'', $Z^{\ominus''}$, m, y and q are as defined above.

Also included among the compounds of formula I are the compounds of subclass Ib:

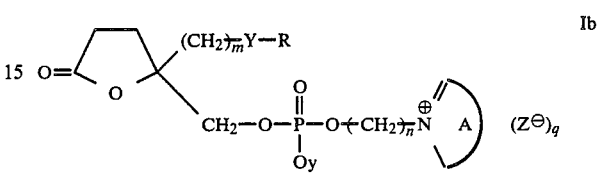

where R, Y, A, $Z^{\ominus}$, m, n, y and q are as defined above.

The preferred compounds of subclass Ib are compounds of formula Ib':

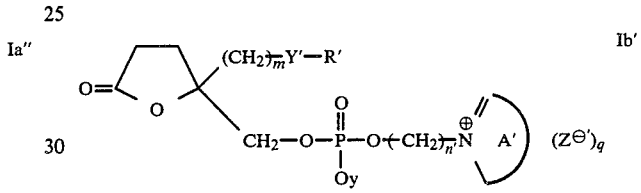

where R', Y', A', $Z^{\ominus'}$, m, n', y and q are as defined above.

The more preferred compounds of subclass Ib are compounds of formula Ib'':

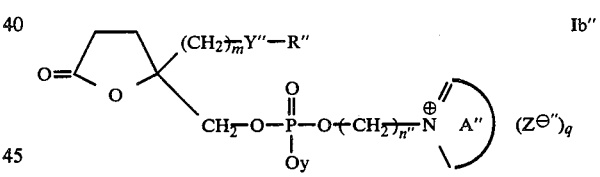

where R'', Y'', A'', $Z^{\ominus''}$, m, n'', y and q are as defined above.

The even more preferred compounds of subclass Ib are compounds of formula Ib''':

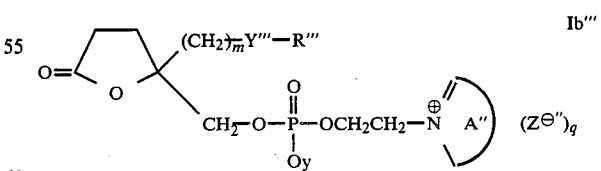

where R''', Y''', A'', $Z^{\ominus''}$, m, y and q are as defined above.

The compounds of subclass Ia where Y is $CH_2$ or O, y is $\ominus$(q is O) and R, A, m and n are as defined above may be prepared by an eight-step reaction as set forth below:

STEP 1

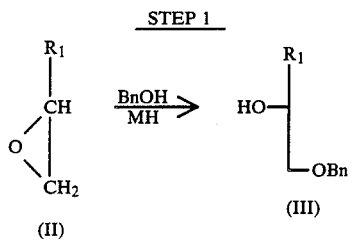

where $R_1$ is n-$C_{14}$-$C_{23}$ alkyl, alkenyl or alkynyl, $CH_2OR$ or $CH_2CH_2OR$, Bn is benzyl, M is an alkali metal or an alkaline earth metal cation and R is as defined above.

STEP 2

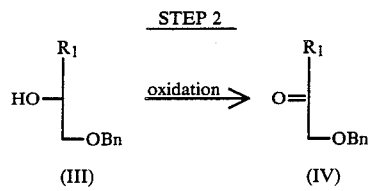

where $R_1$ and Bn are as defined above.

STEP 3

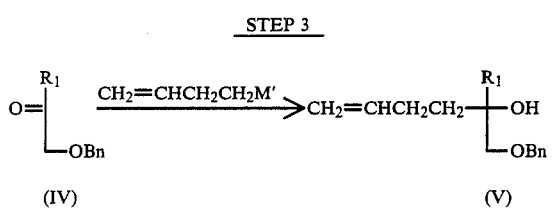

where M' is an alkali or alkaline earth metal and $R_1$ and Bn are as defined above.

STEP 4

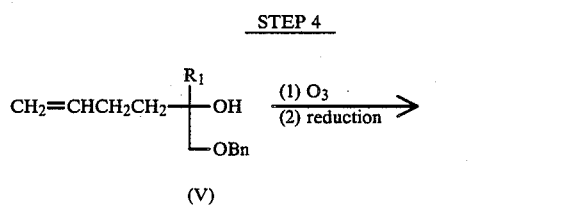

STEP 5

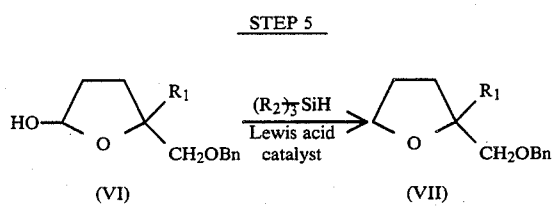

where $R_1$ and Bn are as defined above and $R_2$ is n-$C_1$-$C_4$ alkyl.

STEP 6

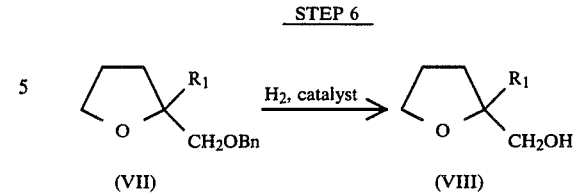

where $R_1$ and Bn are as defined above.

STEP 7

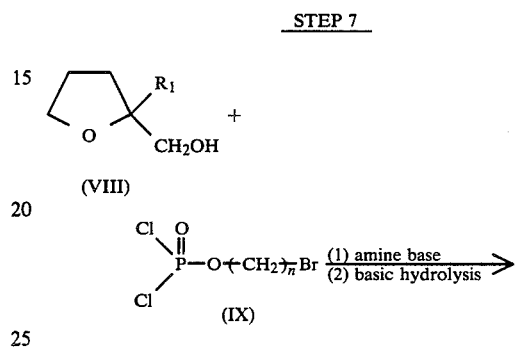

where $R_1$ and n are as defined above.

STEP 8

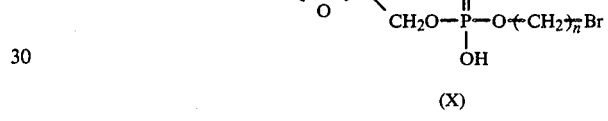

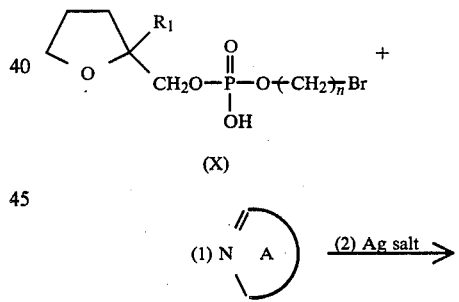

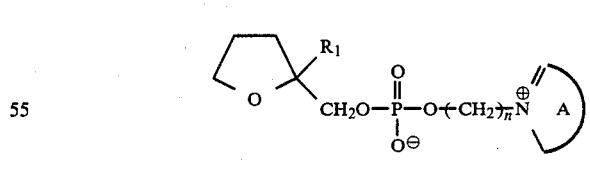

where R, n and A are as defined above.

With respect to the individual steps, Step 1 concerns the reaction of an epoxide of formula II with benzyl alcohol in the presence of an alkali metal or alkaline earth metal hydride, preferably an alkali metal hydride, more preferably sodium hydride, to yield an adduct of formula III. The reaction is conveniently carried out in an inert, organic solvent, e.g., a dialkyl amine such as dimethylformamide or dimethylacetamide, an aromatic hydrocarbon such as toluene, benzene or xylene, a cyclic ether such as tetrahydrofuran, or a mixture thereof. The reaction may be carried out at temperatures of from 30° to 100° C. for a period of 1 to 24 hours.

Step 2 involves the oxidation of a compound produced in Step 1, i.e., a compound of formula III, employing a chromium-based oxidant such as pyridinium chlorochromate to yield a compound of formula IV. The oxidation is carried out in an inert, organic solvent, e.g., a chlorinated hydrocarbon such as methylene chloride, at a temperature of from 20° to 40° C. for a period of between 6 and 36 hours.

Alternatively, the oxidation of a compound of formula III may be carried out employing an oxidant prepared by the action of an activating agent such as an anhydride, e.g., trifluoroacetic anhydride, or an acid chloride, e.g., oxalyl chloride, on a dialkyl sulfoxide, preferably dimethyl sulfoxide, in the presence of an inert, organic solvent, e.g., a chlorinated hydrocarbon such as methylene chloride or an aromatic hydrocarbon such as toluene or xylene, at a temperature of from −78° to 25° C., preferably −78° to 0° C., followed by reaction with a $C_{1-3}$ trialkylamine, e.g., triethylamine, at a temperature of from 0° to 25° C. for a period of between 1 and 3 hours.

As to Step 3, after the preparation of an organometallic reagent by the action of an alkali or alkaline earth metal, e.g. Li or Mg, on an appropriate haloalkene such as 4-bromo-1-butene, in the presence of an aliphatic ether or a cyclic ether such as tetrahydrofuran at a temperature of from 20° to 65° C. for a period of 30 minutes to 2 hours, the organometallic compound is reacted with a compound producted in Step 2, i.e., a compound of formula IV, to yield an olefin of formula V. The reaction is conducted in the presence of the same solvent employed in preparing the organometallic reagent or a mixture of said solvent with a compatible inert organic solvent such as pentane, hexane and the like. The reaction is carried out at a temperature of −78° to 20° C. for a period of between 30 minutes and 18 hours.

Step 4 involves subjecting a compound produced in Step 3, i.e., an olefin of formula V, to ozone in a stream of oxygen in the presence of an inert, organic solvent, e.g., a chlorinated hydrocarbon such as methylene chloride, at a temperature of from −78° to −50° C. until consumption of the olefin has been effected, after which time a reducing agent, preferably a trialkyl phosphite or dialkyl sulfide, e.g., dimethylsulfide, is added. The reduction is carried out at temperatures of from 20° to 30° C. for a period of between 1 and 24 hours to yield a compound of formula VI.

In Step 5, a compound produced in Step 4, i.e., a compound of formula VI, is reacted with a lower trialkyl silane such as triethylsilane and a Lewis acid catalyst, preferably borontrifluoride etherate, to yield a compound of formula VII. The reaction is usually conducted in the presence of a neutral solvent, e.g., a chlorinated hydrocarbon such as dichloromethane, at temperatures of from −30° to 0° C. for a period of between 1 and 4 hours.

Step 6 involves the hydrogenolysis of the benzyl ether group of a compound produced in Step 5, i.e., a compound of formula VII, by dissolving said compound in a lower alkanol, e.g., methanol, ethanol and the like, or a mixture of a lower alkanol and water (up to 15%), with palladium, palladium hydroxide or platinum on carbon and subjecting the resultant mixture to a pressure of between 15 and 65 lbs. of hydrogen gas at a temperature of from 20° to 50° C. for a period of between 5 and 20 hours to yield a compound of formula VIII.

Step 7 is directed to the reaction of a compound produced in Step 6, i.e., a compound of formula VIII, with a compound of formula IX, i.e., a bromoalkoxy-dichlorophosphate compound, e.g., 2-bromoethoxy-dichlorophosphate, in the presence of an amine base, such as pyridine or triethylamine. The reaction is conveniently carried out in an inert, organic solvent, e.g., an aromatic hydrocarbon such as toluene, benzene or xylene, a halogenated aliphatic hydrocarbon, such as methylene chloride, chloroform or carbon tetrachloride, a halogenated aromatic hydrocarbon, e.g., chlorobenzene, or an ether such as diethyl ether. The reaction may be carried out at temperatures of from 20° to 70° C. for a period of between 5 and 30 hours.

The second reaction in Step 7 involves subjecting the product produced in the first reaction to basic hydrolysis, e.g., by suspending the product in water. The hydrolysis is conveniently carried out at a temperature of from 20° to 100° C. for a period of from 15 minutes to about 6 hours to yield a compound of formula X.

The last step, viz., Step 8, is concerned with the conversion of a compound produced in Step 7, i.e., a compound of formula X, into its corresponding cyclimmonium salt by reaction with a compound of formula XI, i.e., an optionally substituted 5- or 6-membered monocyclic or 10-membered bicyclic compound. The reaction producing the cyclimmonium salt, i.e., a compound of formula XII, is optionally conducted in the presence of an aromatic hydrocarbon such as benzene or toluene, a lower alkyl nitrile such as acetonitrile or a polar aprotic solvent such as dimethyl formamide. As to reaction conditions, the reaction is generally carried out at a temperature of from 50° to 100° C. usually in a sealed reaction vessel, for a period of between 12 and 72 hours to yield a hydrobromide salt.

In a second part, the hydrobromide salt prepared in the first part, is treated with a silver salt, e.g., silver carbonate, in the presence of a lower alkanol, e.g., methanol, at a temperature of from 0° to 40° C. for a period of between 15 minutes and 3 hours to yield a compound of formula XII. If the compound of formula XII desired is an unsubstituted pyridinium salt, it is preferred to use pyridine itself as both the reactant and solvent in the first part, in which case the reaction can be carried out at a temperature of from about 20° to 85° C. for a period of between 6 and 24 hours.

When a compound of subclass Ia is desired where R is alkyl, alkenyl or alkynyl, Y is —O—, y is $\ominus$(q is O) and A, m and n are as defined above, it has been found more convenient to employ a three-step reaction commencing with the following reaction:

STEP 1A

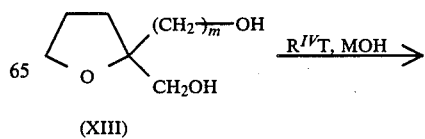

(XIII)

STEP 1A -continued

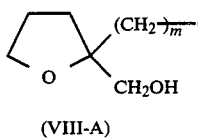

(VIII-A)

where $R^{IV}$ is n-$C_{12}$-$C_{20}$ alkyl, alkenyl or alkynyl, T is chloro, bromo or iodo and M and m are as defined above. In Step 1A, a diol of formula XIII is reacted with a halo ($C_{14}$-$C_{18}$) alkane, alkene or alkyne, e.g., 1-bromooctadecane, in the presence of an alkali metal or alkaline earth metal hydroxide, preferably an alkali metal hydroxide, to yield a compound of formula VIII-A. The reaction is conveniently carried out in the presence of an inert, organic solvent, e.g., a dialkyl amide such as dimethylformamide or dimethylacetamide, an aromatic hydrocarbon such as toluene, benzene or xylene, or a mixture of a dialkylamide and an aromatic hydrocarbon. Alternatively, the inert, organic solvent employed may be dimethylsulfoxide, a cyclic ether such as tetrahydrofuran, or a mixture thereof. The reaction may be carried out at temperatures of from 15° to 50° C. for a period of between 1 and 6 hours.

Employing a compound produced in Step 1A, i.e., a compound of formula VIII-A, and carrying out the reactions described above in Steps 7 and 8, results in a compound having the formula

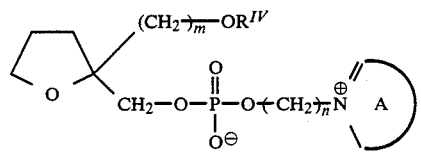

The compounds of subclass Ia where Y is

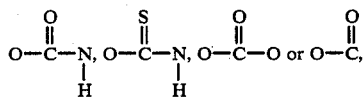

y is ⊖ (q is O) and R, A, m and n are as defined above may be prepared by the following reaction scheme:

REACTION A

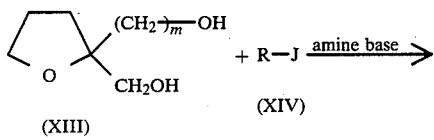

where J is an isocyanate, isothiocyanate, chlorocarbonate or carboxychloride group, and R, Y and m are as defined above.

REACTION B

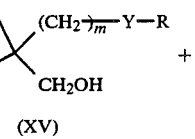

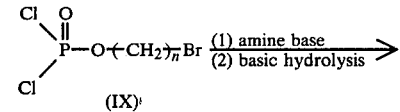

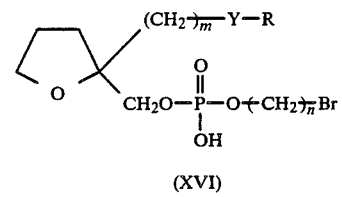

where Y, R, m and n are as defined above.

REACTION C

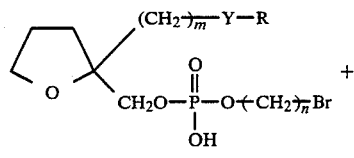

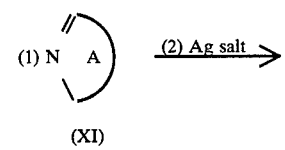

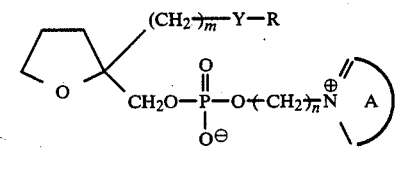

where Y, R, m, n and A are as defined above.

Turning to the reactions individually, Reaction A involves the reaction of a diol compound of formula XIII with a compound of formula XIV, i.e., an appropriate isocyanate, isothiocyanate, chlorocarbonate or carboxychloride compound containing the residue, R, in the presence of an amine base, such as pyridine or triethylamine, to yield a compound of formula XV. The reaction may optionally be conducted in the presence of a cosolvent which may be an aromatic hydrocarbon such as benzene or toluene, an aromatic halohydrocarbon such as chlorobenzene, an aliphatic halohydrocarbon such as chloroform or dichloromethane, a dialkyl ether such as diethylether, a cyclic ether such as tetrahydrofuran or a dialkyl amide such as dimethylformamide. The reaction is typically carried out at a temperature of from 20° to 100° C. for a period of between 1 and 24 hours.

As to Reaction B and Reaction C for preparing a compound of formula XVI and XVII, respectively, they are conducted in essentially the same manner as set forth above in Steps 7 and 8.

The compounds of subclass Ib where Y is $CH_2$ or O, y is $\ominus$ (q is O) and R, A, m and n are defined above may be prepared essentially as described below employing a compound of formula VI as the starting material:

STEP A

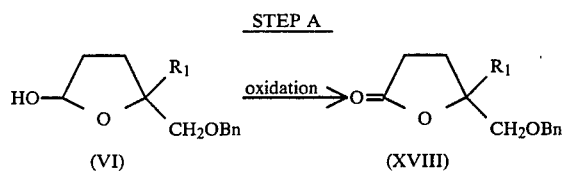

where $R_1$ and Bn are as defined above.

STEP B

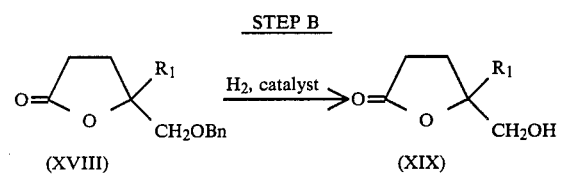

where $R_1$ and Bn are as defined above.

STEP C

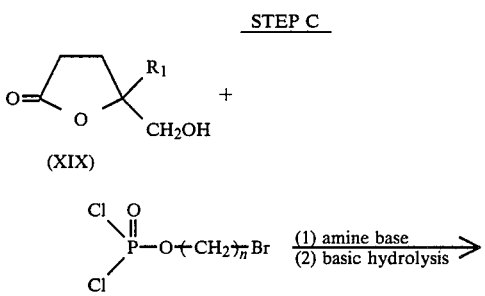

where $R_1$ and n are as defined above.

STEP D

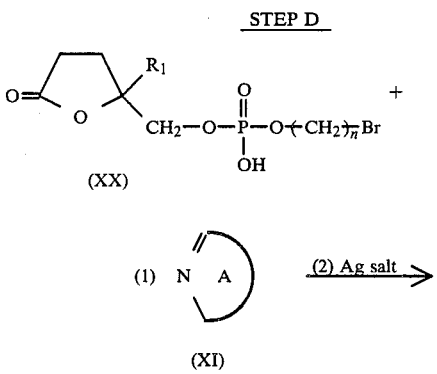

-continued
STEP D

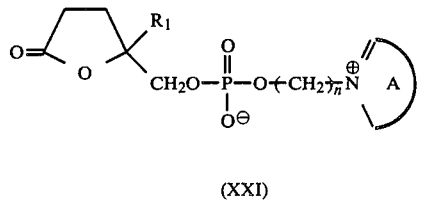

(XXI)

where $R_1$, n and A are as defined above.

In considering the steps individually, Step A concerns the oxidation of a compound of formula VI to yield a compound of formula XVIII. The oxidation is carried out according to either of the procedures set forth in Step 2 above with regard to the description for preparing the compounds of subclass Ia.

Step B involves the hydrogenolysis of the benzyl ether group of a compound produced in Step A, i.e., a compound of formula XVIII, to yield a compound of formula XIX. The hydrogenolysis is conveniently carried out in accordance with the procedure set forth in Step 6 above with regard to the description for preparing the compounds of subclass Ia.

As to Step C and Step D for preparing a compound of formula XX and XXI, respectively, they are conducted in an analogous manner to that set forth above in Steps 7 and 8 regarding the description for preparing the compounds of subclass Ia.

The compounds of subclass Ib where Y is

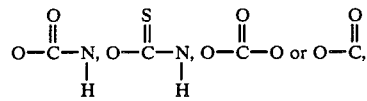

y is $\ominus$ (q is O) and R, A, m and n are as defined above may be prepared by the following reaction scheme:

REACTION AA

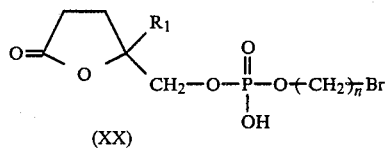

where $R_3$ is $(CH_2—OC(CH_3)_2OCH_3)$, and m, Bn and M are as defined above.

REACTION BB

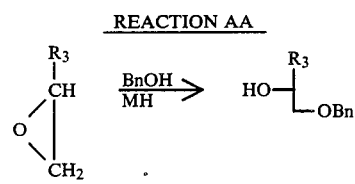

where $R_3$ and Bn are as defined above.

REACTION CC

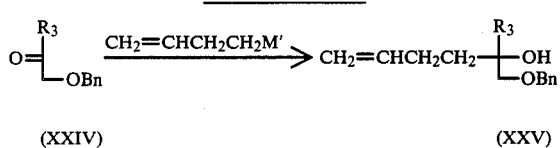

(XXIV)　　　　　　　　　(XXV)

where R$_3$, Bn and M' are as defined above.

REACTION DD

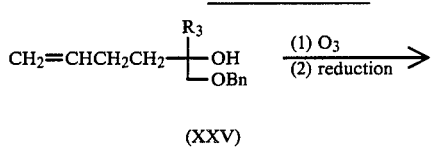

(XXV)

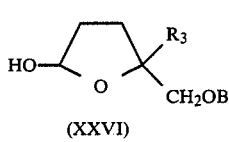

(XXVI)

where R$_3$ and Bn are as defined above.

REACTION EE

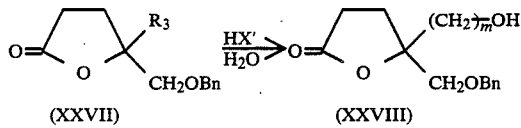

(XXVI)　　　　　　　(XXVII)

where R$_3$ and Bn are as defined above.

REACTION FF

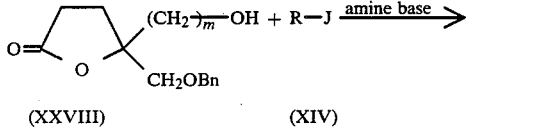

(XXVII)　　　　　　　(XXVIII)

where HX' is a organic acid or a mineral acid, and R$_3$, Bn and m are as defined above.

REACTION GG

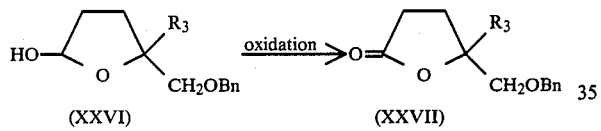

(XXVIII)　　　　(XIV)

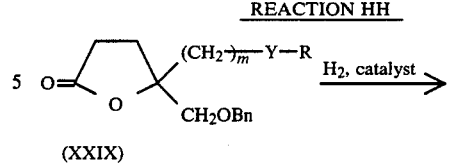

(XXIX)

where Bn, m, R, J and Y are as defined above.

REACTION HH

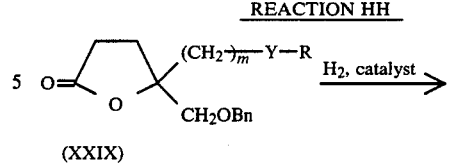

(XXIX)

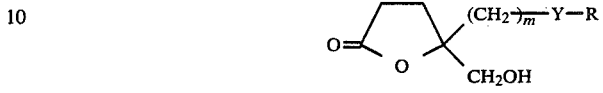

(XXX)

where Bn, m, R and Y are as defined above.

REACTION II

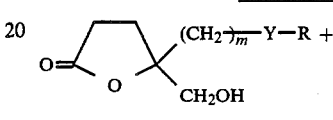

(XXX)

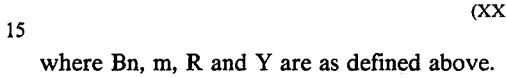

(IX)

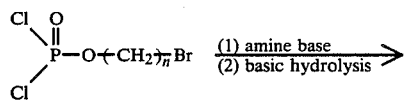

(XXXI)

where m, R, Y and n are as defined above.

REACTION JJ

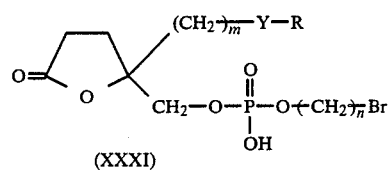

(XXXI)

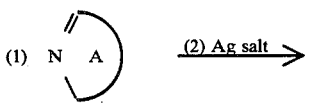

(XI)

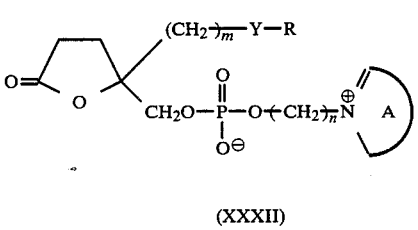

(XXXII)

where m, R, Y, n and A are as defined above.

As to the individual reactions, Reaction AA concerns the reaction of an epoxide of formula XXII with benzyl alcohol in the presence of an alkali metal or alkaline earth metal hydride, preferably an alkali metal hydride, more preferably sodium hydride, to yield an adduct of formula XXIII. With regard to the reaction conditions, i.e., the reaction medium, temperatures employed and reaction times, this reaction is conducted in an analogous manner to that set forth in Step 1 above regarding the description for preparing the compounds of subclass Ia.

Reaction BB involves the oxidation of a compound produced in Reaction AA, i.e., a compound of formula XXIII, to yield a compound of formula XXIV. The oxidation is carried out in accordance with either of the procedures set forth in Step 2 above with regard to the description for preparing the compounds of subclass Ia.

In Reaction CC, a compound produced in Reaction BB, i.e., a compound of formula XXIV, is reacted with an organometallic compound to yield an olefin of formula XXV. As to the nature of the organometallic compound and the reaction conditions, this reaction is carried out in an identical manner to that set forth above in Step 3 directed to the preparation of compounds of subclass Ia.

Reaction DD involves subjecting a compound produced in Reaction CC, i.e., an olefin of formula XXV, to ozone in a stream of oxygen in the presence of an inert, organic solvent, e.g., a chlorinated hydrocarbon at an extremely low temperature, e.g., $-80°$ to $-50°$ C., until the consumption of the olefin has been effected. A reducing agent is then added, preferably a trialkyl phosphite or dialkyl sulfide, and reduction is carried out at ambient temperatures, i.e., in the range of $20°$ to $30°$ C., for a period of between 1 and 24 hours to yield a compound of formula XXVI.

In Reaction EE, a compound produced in Reaction DD, i.e., a compound of formula XXVI, is oxidized employing either of the procedures set forth in Step 2 above regarding the description for preparing the compounds of subclass Ia to yield a compound of formula XXVII.

Reaction FF concerns the reaction of a compound produced in Reaction EE, i.e., a compound of formula XXVII, with a mineral acid such as hydrochloric or sulfuric acid, or an organic acid such as p-toluenesulfonic acid, in the presence of a cosolvent, e.g., a mixture of a cyclic ether such as tetrahydrofuran in water. The reaction is conducted at a temperature of from $0°$ to $25°$ C. for a period of between 30 minutes and 4 hours and yields a compound of formula XXVIII.

Reaction GG involves the reaction of a compound produced in Reaction FF, i.e., a compound of formula XXVIII, with an appropriate isocyanate, isothiocyanate, chlorocarbonate or carboxylchloride compound containing the residue, R, in the presence of an amine base, such as pyridine or triethylamine to yield a compound of formula XXIX. The reaction is conducted in an analogous manner to that set forth in Reaction A above for preparing the compounds of subclass Ia.

Reaction HH concerns the hydrogenolysis of the benzyl ether group of a compound produced in Reaction GG, i.e., a compound of formula XXIX. The hydrogenolysis is conducted in a similar manner to that set forth in Step 6 above regarding the description for preparing the compounds of subclass Ia to yield a compound of formula XXX.

As to Reaction II and Reaction JJ for preparing a compound of formula XXXI and XXXII, respectively, they are conducted in essentially the same manner as that set forth in Steps 7 and 8 regarding the description for preparing the compounds of subclass Ia.

It should be understood that when any of the previously described processes involve the preparation of compounds where R is a functionality sensitive to hydrogenolysis, i.e., alkenyl or alkynyl, the debenzylation should be effected employing a trialkylsilyliodide compound. For example, in the preparation of compounds of subclass Ia where Y is $CH_2$ or O, y is $\ominus$ (q is O) and m and n are as defined above, the debenzylation step may be conducted as depicted below:

STEP 6-A

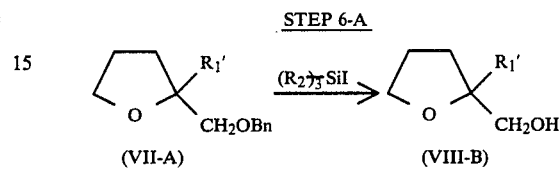

where $R_1'$ is n-$C_{14}$-$C_{23}$ alkenyl or alkynyl, $CH_2OR$ or $CH_2CH_2OR$ where R is n-$C_{12}$-$C_{20}$ alkenyl or alkynyl, and Bn and $R_2$ are as defined above.

As to the reaction conditions, Step 6-A involves the reaction of a compound of formula VII-A with a trialkylsilyliodide compound, preferably trimethylsilyliodide, to yield a compound of formula VIII-B. The reaction is optionally conducted in the presence of a cosolvent, e.g., an aromatic hydrocarbon such as benzene or toluene, or a lower alkyl nitrile such as acetonitrile, at a temperature of from $20°$ to $110°$ C. for a period of between 1 and 24 hours.

The compounds of formulae II, IX, XI, XIII, XIV and XXII are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile) or fractional distillation under high vacuum (if sufficiently volatile). Often, however, the crude product of one reaction may be employed in the following reaction without purification.

As is evident to those skilled in the art, the compounds of formula I can exist in racemic or enantiomeric form and both forms are contemplated as being included within the scope of this invention.

Moreover, and as is also evident to those skilled in the art from structural formula I, said formula not only embraces the inner salts, i.e., compounds of formula I where y is $\ominus$ (q is O), but also the pharmaceutically acceptable acid addition salts (i.e., those salts which do not significantly increase the toxicity of the base compound), i.e., compounds of formula I where y is H (q is 1). The compounds of formula I can be converted into acid addition salt form in conventional manner. In this connection, and with regard to the processes described above for preparing all of the compounds of formula I, it can be clearly seen that the hydrobromide salts of all of the end-products, described above, e.g., the hydrobromide salt of a compound of formula XII, can be prepared by omitting the second part of Step 8 and recovering the product produced in the first part.

All of the compounds of formula I are useful as platelet activating factor inhibitors as indicated by their ability to inhibit platelet activating factor (PAF)-induced human platelet aggregation in vitro according to the Platelet Aggregation Inhibition Assay test (PAIA test) as follows:

Human subjects are kept aspirin free for one week and fasted overnight. Platelet rich plasma (PRP) is prepared by centrifugation (200×g.) of freshly drawn blood, anti-coagulated with 0.38% sodium citrate (final concentration). Platelet count is adjusted to 250,000 per $\mu$l using platelet poor plasma (PPP) obtained by a second centrifugation (700×g.) of the blood sample. An aliquot (0.38 ml.) of the PRP is dispensed into cuvettes and maintained at room temperature (22° C.) until used (but for not more than two hours). The PRP-containing cuvettes are incubated at 37° C. and stirred at 900 rpm within a Payton Aggregometer which is activated to follow the light deflection pattern prior to the addition of the test compound. The test compound (dissolved in a suitable solvent mixture which does not influence platelet aggregation) is then added to a PRP-containing cuvette in an amount sufficient to provide a final concentration of 100 $\mu$M. Between one and two minutes after the addition of the test compound, the aggregation inducing agent (C-16 PAF-Sandoz-Hanover), dissolved in a buffer consisting of 0.01M Tris-Tyrodes buffer with 0.25% bovine serum albumin (pH 7.4), is added to the PRP-containing cuvettes in an amount predetermined to give a consistent aggregation response (either 0.1 $\mu$M or 0.01 $\mu$M). All aggregations are allowed to proceed for 6 minutes from the addition of the inducing agent. The aggregation response is quantitated by determining the area under the curve (AUC). The AUC calculated for the inducing agent alone is considered to be one hundred percent. The potential percent inhibition of the aggregation response is determined by dividing the AUC generated in the presence of the compound by the AUC of the inducing agent alone, multiplying by 100 and then subtracting from 100. The compounds demonstrating greater then 50% inhibition at 100 $\mu$M are evaluated at lower concentrations to generate an $IC_{50}$ (50% inhibitory concentration) value.

Moreover, it has been found that all of the compounds of formula I are useful as platelet activating factor receptor antagonists as indicated by their ability to inhibit specific binding of [$^3$H]-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 $\mu$g/ml of Prostaglandin I$_2$ (PGI$_2$) in a ratio of blood to anti-coagulant of 9:1. Platelet rich plasma (PRP) is prepared by centrifugation (250×g) of the blood for 20 minutes at room temperature. The PRP is then centrifuged (900×g) for 10 minutes at room temperature and the platelet pellet is washed two times with Tris-Tyrode's (TT) solution having a pH of 7.4 and containing 0.25% bovine serum albumin (BSA), and to which has been added PGI$_2$ at a final concentration of 0.3 g/ml. The platelets are resuspended at 350,000 $\mu$l in TT/BSA containing 1.4 mM CaCl$_2$.2H$_2$O and 0.7 mM MgCl$_2$.6H$_2$O. All of the tests are conducted in duplicate and each of the test compounds is evaluated at concentrations of 100, 50, 1 and 0.1 $\mu$M. For each determination, the following solutions are mixed:

500 $\mu$l of the above-described platelets;

10 $\mu$l of [$^3$H]-PAF (40,000 counts per minute (cpm) to a final concentration of 1.5 $\mu$M); and
either 10 $\mu$l of the test compound at 50× the desired final concentration, 10 $\mu$l of vehicle (total bound), or 10 $\mu$l of 1.85×10$^{-5}$M cold PAF (non-specifically bound).

Each mixture is allowed to incubate at room temperature for one hour, after which time the reaction is terminated by the addition of 500 $\mu$l of ice cold TT/BSA and centrifugation (900×g) at 4° C. for 10 minutes. The resultant supernatant is aspirated into scintillation vials and the pellet is washed with 250 ml. of ice cold TT/BSA and centrifuged (900×g) at 4° C. for 10 minutes. The supernatants are then aspirated into the same scintillation vials as before and 10 ml. of Scintiverse II (a liquid scintillation cocktail) is added to and mixed therewith. The pellets are resuspended in 500 $\mu$l of Scintiverse II and mixed well. An additional 2 ml. of Scintiverse II is then added to the vials and, after mixing, the vials are counted for 1 minute in a liquid scintillation spectrometer. The amount of specific binding is calculated as the difference in cpm between the total bound [$^3$H]-PAF and non-specifically bound [$^3$H]-PAF. The percent inhibition of specific binding is determined by dividing the cpm specifically bound in the presence of the test compound by the cpm specifically bound in total, multiplying by 100 and then subtracting from 100. An $IC_{50}$ (50% inhibitory concentration) value is generated by evaluating the test compound over the full concentration range.

Furthermore, in view of their usefulness as PAF receptor antagonists, the compounds of formula I have been found useful as inhibitors of PAF-mediated bronchoconstriction, which property was evaluated by the PAF-induced Pulmonary Inflation Pressure (PIP) Increase test (Test B) as follows:

Male guinea pigs, weighing between 300 and 400 gm, are anesthetized, after which time trachea tube, carotid and jugular catheters are inserted. The test animal is then force ventilated employing a small animal Harvard respirator and the resistance to lung inflation (PIP) is measured utilizing a pressure transducer and recorder. The test compound is administered either orally at 30 minutes prior to or intravenously (jugular) at 5 minutes prior to the introduction of PAF. The PAF (C$_{18}$-Sandoz, Hanover) is dissolved in Tris-Tyrode's bovine serum albumin buffer and administered intravenously (jugular) at 100 ng/kg. Any blood pressure measurements taken are recorded from a transducer attached to the carotid catheter. Two responses are noted in the PIP recordings after the PAF is administered: (1) an immediate response which, in PAF-only treated test animals, averages out to between 70% and 80% more than the baseline PIP values. (This early response is also the greatest response and is, therefore, termed maximal PIP); and (2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been administered PAF and the test compound compared to the test animal to which only PAF has been administered.

Still further, the compounds of formula I are useful as inhibitors of PAF-mediated extravasation (the extrusion of plasma from the lumen of the blood vessels into the vessel wall and surrounding tissues) measured as a function of hemoconcentration according to the PAF-induced Extravasation test (Test C) as follows.

Male guinea pigs, weighing between 300 and 400 gm, are anesthetized, after which time a femoral catheter is inserted. The test compound is administered intraarterially at one to five minutes prior to the introduction of PAF. The PAF ($C_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 $\mu$l heparinized hematocrit tubes. These samples are taken just prior to the injection of PAF, one minute subsequent to the injection of PAF and every two minutes thereafter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hematocrit values obtained with the test compound are compared to the hemoconcentration values obtained with PAF alone and are expressed as percent inhibition of percent increase in hematocrit.

Yet still further, the compounds of formula I are useful as inhibitors of PAF-induced hypotension as measured by their ability to inhibit the lowering of blood pressure levels induced by PAF according to the following test (Test D):

Male Wistar rats, weighing approximately 300 gm, are anesthetized and their carotid arteries cannulated to enable their diastolic and systolic arterial blood pressure measurements to be recorded. PAF is then administered intravenously at either 100 or 500 ng/kg, and the blood pressure drop (within 10 sec.) and recovery time required to reach the pre-injection blood pressure level are measured. At 100 ng/kg, a 30% decrease in blood pressure and a 3 to 4 minute recovery time are observed, whereas at 500 ng/kg, a 52% decrease in blood pressure and a 10 minute recovery time are observed. In order to measure the effectiveness of a compound for both the inhibition of blood pressure decreases and shortening of the recovery time, the test compound is administered intravenously over a range of between 5 and 7 dosage levels (1 or 2 test animals per dose) and between 1 and 5 minutes prior to the introduction of PAF to generate an $ED_{50}$.

Yet even still further, the compounds of formula I are useful as inhibitors of PAF-induced ischemic intestinal necrosis, which property was measured in accordance with the following test (Test E):

Following essentially the procedure of F. Gonzalez-Crussi and W. Hsueh published in J. Amer. Pathol., 112, pgs. 127–135 (1983), male Sprague-Dawley rats, weighing approximately between 260 and 300 g, are anesthetized and their carotid arteries cannulated and connected to a blood pressure transducer and recorder. The test compound is introduced into a cannula inserted into the jugular vein at a time 10 minutes prior to the administration of PAF. The abdomen is then incised along the midline and 2 $\mu$g of PAF or 20 $\mu$g of LPS (lipopolysaccharide) immediately followed by 1 $\mu$g of PAF are injected into the abdominal aorta at the level of the renal artery. The abdominal incision is then covered with saline-moistened gauze and the intestine exposed and examined periodically up to 2 to 3 hours prior to sacrifice. Into the jugular vein is then injected 5 ml of 2% Evans Blue to assess the degree of intestinal perfusion. Blocks of intestinal tissue are then taken for microscopic examination to determine either the extent of necrosis or to verify the absence of necrosis when inhibited by the test compound. Microscopic changes in the intestine are assessed by hematoxylin and eosin staining. The test compound is assessed for its ability to alleviate or prevent the development of gross and microscopic lesions and may be expressed in terms of the number of animals in which inhibition is observed relative to the control (taken to be 100%).

The compounds of formula I may be combined with one or more pharmaceutically, acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The precise dosage of a compound of formula I to be employed for inhibiting platelet activating factor (PAF) depends upon several factors including the host, the nature and the severity of the condition being treated, the mode of administration and the particular compound employed. However, in general, satisfactory inhibition or antagonism of platelet activating factor is achieved when a compound of formula I is administered orally at a daily dosage of 0.05–100, preferably 0.1–30 mg/kg body weight or, for most larger primates, daily dosage of 1–500 mg, preferably 1–50 mg. A typical oral dosage is 5 mg, three times a day.

As with the PAF inhibition use, the precise dosage of a compound of formula I to be employed in treating platelet activating factor mediated bronchoconstriction and extravasation, platelet activating factor induced hypotension and ischemic bowel disease depends upon several factors including the host, the nature and severity of the condition being treated, the mode of administration and the particular compound employed. However, in general, satisfactory inhibition or antagonism of platelet activating factor mediated bronchoconstriction and extravasation, platelet activating factor induced hypotension and ischemic bowel disease is achieved when a compound of formula I is administered orally at a daily dosage of 0.2–100, preferably 0.2–50 mg/kg body weight or, for most larger primates, a daily dosage of 10–2000 mg, preferably 10–350 mg. A typical oral dosage is 50 or 100 mg, two or three times a day.

Regardless of use, a small dosage is gradually increased until the optimal dosage for the host under treatment is determined. For administration by injection, a dosage somewhat lower than would be used for oral administration of the same compound to the same host having the same condition is usually employed.

The compounds of formula I may be formulated into such pharmaceutical compositions containing an amount of the active substance that is effective for inhibiting PAF, in treating PAF mediated bronchoconstriction and extravasation, in treating PAF-induced hypotension, or in treating ischemic bowel disease, such compositions in unit dosage form and such compositions comprising a solid pharmaceutically acceptable carrier.

Tablets and capsules containing the ingredients indicated below may be prepared by conventional techniques and are useful as platelet activating factor inhibitors. The tablet may be administered once or twice a day whereas the capsule is suitably administered three times a day.

| Ingredients | Weight (mg) tablet | capsule |
| --- | --- | --- |
| compound of formula I, e.g. the compound of Example 3 | 5 | 5 |
| tragacanth | 10 | — |
| lactose (spray-dried) | 257.5 | 95 |
| corn starch | 15 | — |
| talcum | 10 | — |
| magnesium stearate | 2.5 | — |
| Total | 300.0 | 100 |

The following are representative of tablets and capsules which may be prepared by conventional means and are useful in treating platelet activating factor mediated bronchoconstriction and extravasation, platelet activating factor induced hypotension and ischemic bowel disease. The tablet and the capsule may be suitably administered two or three times a day.

| Ingredients | Weight (mg) tablet | capsule |
| --- | --- | --- |
| compound of formula I, e.g., the compound of Example 3 | 50 | 50 |
| tragacanth | 10 | — |
| lactose (spray-dried) | 212.5 | 100 |
| cornstarch | 15 | — |
| talcum | 10 | — |
| magnesium stearate | 2.5 | — |
| Total | 300.0 | 150.0 |

The following examples show representative compounds encompassed by this invention and their synthesis. However, it should be clearly understood that they are for purposes of illustration only.

EXAMPLE 1

3-[2-[(2-Octadecyloxy)ethyl-5-oxo-tetrahydrofuran-2-yl]methoxyhydroxyphosphinyloxy-ethane]thiazolium hydroxide-inner salt-4-oxide

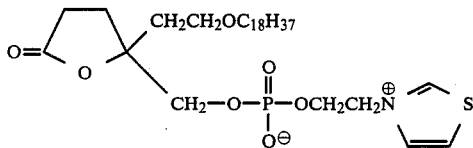

(a) Preparation of 1-benzyloxy-4-octadecyloxy-butane-2-ol

To 12.0 g of 60% sodium hydride in mineral oil (30 mmol, washed free of oil by the use of petroleum ether) was added 32.4 g (0.3 mol) of benzyl alcohol in 200 ml of dry dimethylformamide. The suspension was heated under a flow of nitrogen to 80° C. and maintained at this temperature for 45 minutes, after which time 66.1 g (0.19 mol) of an epoxide (prepared by the peracid oxidation of octadecyl-3-butenyl ether) in 100 ml of dimethylformamide was added and the temperature maintained at 80° C. for 15 hours. The solvent was then removed in vacuo and the residue chromatographed on silica gel employing a mixture of petroleum ether and diethyl ether in a ratio of 3:2 as the eluent to yield a wax-like solid.

(b) Preparation of 1-benzyloxy-4-octadecyloxy-2-butanone

To a complex prepared at −60° C. from the addition of 10.4 ml of dry dimethyl sulfoxide to 8.9 g (70 mmol) of oxalyl chloride in 150 ml of methylene chloride, was added, dropwise, 27.7 g (62.2 mmol) of the compound prepared in (a) above. After stirring the mixture under a nitrogen atmosphere for 1 hour, 50 ml of triethylamine in 50 ml of methylene chloride was added and the resultant mixture was allowed to warm to 0° C. over a period of 30 minutes, after which time it was quenched with 75 ml of water. After the mixture was allowed to warm to room temperature, the organic layer was separated, washed with a saturated sodium chloride solution, dried over magnesium sulfate and concentrated in vacuo to afford an oil which solidified on standing. Flash chromatography on silica gel employing a mixture of petroleum ether and diethyl ether in a ratio of 7:3 as the eluent yielded a solid, m.p. 33°–34° C.

(c) Preparation of 3-benzyloxymethyl-3-hydroxy-1-octadecyloxy-hept-6-ene 1.12 g (8 mmol) of 4-bromo-1-butene in 15 ml of dry ether was reacted with 200 mg of magnesium turnings at reflux under a nitrogen atmosphere for 1 hour. The resulting Grignard reagent was cooled to −60° C. and then treated with 2.22 g (5 mmol) of the compound prepared in (b) above in 30 ml of ether. After 1 hour at −60° C., the mixture was warmed overnight to room temperature and then quenched with a saturated aqueous ammonium acetate solution and partitioned. The organic layer was then washed twice with ammonium acetate, washed with a saturated sodium chloride solution and dried over magnesium sulfate, after which time the solvent was removed under reduced pressure. Purification of the crude product was effected on silica gel employing a mixture of petroleum ether and diethyl ether as the eluent to yield a low melting solid.

(d) Preparation of 5-benzyloxymethyl-2-hydroxy-5-(2-octadecyloxyethyl)-tetrahydrofuran 6.15 g (12.3 mmol) of the compound prepared in (c) above in 100 ml of methylene chloride was treated with ozone at −60° C. After consumption of the olefin, 25 ml of dimethyl sulfide was added and the mixture allowed to warm to room temperature. The solvent was removed in vacuo and the crude product was purified on silica gel employing a mixture of petroleum ether and diethylether in a ratio of 7:3 as the eluent to yield a colorless oil.

(e) Preparation of 5-benzyloxymethyl-5-(2-octadecyloxyethyl)-4,5-dihydro-2(3H)-furanone To a solution of 1.6 g (7.4 mmol) of pyridinium chlorochromate in 25 ml of methylene chloride under a nitrogen atmosphere, was added 13.5 g (6.5 mmol) of the compound prepared in (d) above in 25 ml of methylene chloride. After 18 hours at 25° C., the solution was diluted with 150 ml of ether, filtered through silica gel and the filtrate evaporated to afford an oil. The oil was then flash chromatographed on silica gel employing a mixture of petroleum ether and diethyl ether in a ratio of 7:3 as the eluent to yield colorless oil.

(f) Preparation of 5-hydroxymethyl-5-(2-octadecyloxyethyl)-4,5-dihydro-2(3H)furanone A mixture containing 10.2 g (21.83 mmol) of the compound prepared in (e) above, 300 ml of a mixture of ethyl alcohol and water in a ratio of 9:1 and 1.5 g of 5% palladium on carbon (50% water content) was placed in a pressure bottle and hydrogenated at 40° C. under a pressure of 50 lbs. of hydrogen until uptake was complete. The catalyst was then filtered off and the filtrate concentrated in vacuo. The residue was crystallized from methanol to yield a solid.

(g) Preparation of 2-bromoethyl-[(2-octadecyloxyethyltetrahydro-5-oxo-furan-2-yl)-methyl]phosphoric acid diester To 14 g (33.9 mmol) of the compound prepared in (f) above in 60 ml of dry benzene was added 9.9 g (40.7 mmol) of 2-bromoethyloxyphosphoro-dichloridate. The resultant solution was cooled on in ice-salt bath and treated dropwise, under a nitrogen atmosphere, with a solution of 3.5 ml of pyridine in 40 ml of benzene. After the ice-salt bath was removed, the mixture was allowed to warm to room temperature over a period of 6 hours. The volatiles were removed under reduced pressure and the residue was suspended in 500 ml of water and heated on a steam bath for 80 minutes. After cooling to room temperature, the mixture was extracted with chloroform. The extract was dried over magnesium sulfate, filtered and, after removal of the solvent, a white solid was obtained.

Preparation of the title compound

The compound prepared in (g) above was placed into a pressure bottle and 22 g of thiazole in 20 ml of toluene was added. The resultant mixture was heated at 65° C. for 50 hours, after which time it was cooled and evaporated in vacuo. The residue was then taken up with 500 ml of methanol and, after the addition of 10.5 g of silver carbonate, the mixture was stirred for 90 minutes. The solids were then removed by filtration and the filtrate evaporated under reduced pressure to yield the crude product as a brown residue. The crude product was then purified on silica gel and eluted successively with a 5% solution of methanol in methylene chloride, a 20% solution of methanol in methylene chloride and finally a solution of methylene chloride, methanol and water in a ratio of 10:5:1 to yield the title compound as a white solid, m.p. 200°–205° C. (dec.)

PAIA test—IC$_{50}$—10.5 μM
TEST A—IC$_{50}$—1.8 μM
TEST C—ED$_{50}$—0.25 mg/kg (ia)

EXAMPLE 2

3-[2-[(2-Octadecyloxymethyltetrahydrofuran-2-yl-methoxy)-hydroxyphosphinyloxy]-ethane]-thiazolium hydroxide inner salt-4-oxide

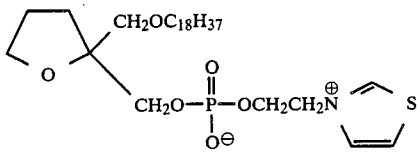

(a) Preparation of 2-hydroxymethyl-2-octadecyloxymethyl tetrahydrofuran

To a mixture of 2.64 g (20 mmol) of 2,2-bishydroxymethyl tetrahydrofuran and 2.20 g (6.6 mmol) of 1-bromooctadecane in 8 ml of a dimethylsulfoxide-tetrahydrofuran solution in a 1:1 ratio was added 1.84 g (26.4 mmol) of finely powdered potassium hydroxide and the resultant mixture was stirred at room temperature for 2 hours. The mixture was then poured into 100 ml of water, diluted with a saturated sodium chloride solution and extracted with ether. The ether extract was then washed with saturated sodium chloride and dried over sodium sulfate. The solvents were then removed to yield the crude product as a low-melting solid. The crude product was then chromatographed on silica gel employing methyl-t-butyl ether and hexane in a 3:1 ratio as the eluent to yield a white, waxy solid.

(b) Preparation of 2-bromoethyl-[(2-octadecyloxymethyltetrahydrofuran-2-yl)-methyl]phosphoric acid diester To 0.244 g of bromoethoxyphosphordichloridate in 2.5 ml of benzene was added 0.322 g (0.84 mmol) of the compound prepared in (a) above and, after cooling the resultant mixture on an ice bath, the cooled mixture was treated dropwise with 82 μl of dry pyridine. The ice bath was then removed and the mixture stirred, under a nitrogen atmosphere, for 5 hours. The solvent was then removed in vacuo and to the residue was added 4 ml of water. The mixture was then heated on a steam bath for 15 minutes, then cooled to room temperature, diluted with water and extracted with ether. The ether extracts were then washed with water, dried over sodium sulfate and, after removal of the solvents, a foam was obtained.

Preparation of the title compound

To a pressure bottle containing 1 ml of a mixture of thiazole and toluene in a 1:1 ratio was added the compound prepared in (b) above and, after sealing the bottle, the mixture was heated for 6 days. The volatiles were then removed in vacuo and the residue was then taken up in ethanol. 0.5 g of silver carbonate was then added and the mixture stirred for 1 hour, after which time it was filtered through Celite and the filtrate evaporated to dryness. To the resultant residue was added 10 ml of methanol and 100 mg of activated charcoal and the mixture was then heated for 5 minutes at 50° C. The solids were then removed by filtration and the filtrate evaporated under reduced pressure to yield the crude product. The crude product was then purified on silica gel in a manner analogous to that described above in Example 1 to yield the title compound as a solid, m.p. >140° C. (dec.)
PAIA test—IC$_{50}$—81.5 μM
TEST A—IC$_{50}$—3.3 μM
TEST C—54% inh. at 2.8 mg/kg (ia)

EXAMPLE 3

3-[2-[(2-Octadecylaminocarbonyloxymethyl tetrahydrofuran-2-yl-methoxy)-hydroxyphosphinyloxy]-ethane]-thiazolium hydroxide inner salt-4-oxide

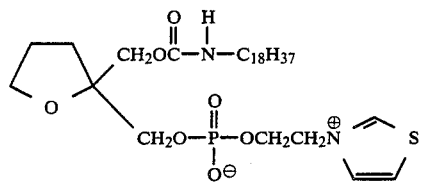

(a) Preparation of 2-hydroxymethyl-2-octadecylaminocarbonyloxy tetrahydrofuran To a mixture of 1.9 g (14.4 mmol) of 2,2-bishydroxymethyl tetrahydrofuran in 10 ml of pyridine was added, at room temperature and under a nitrogen atmosphere, a solution of 4.04 g (13.7 mmol) of n-octadecylisocyanate in 15 ml of pyridine. The resultant mixture was heated to 60° C. and maintained at this temperature for 3 hours, after which time the solvent was removed in vacuo to yield a residue which was partitioned in a mixture of methylene chloride and 2N hydrochloric acid. The organic layer was then washed successively with saturated sodium chloride, 2N hydrochloric acid, saturated sodium bicarbonate and saturated sodium chloride and dried over magnesium sulfate. The solvent was then removed and the residue chromatographed on silica gel employing methyl-t-butyl ether as the eluent to yield a white solid.

(b) Preparation of 2-bromoethyl-[(2-octadecylaminocarbonyloxymethyl-tetrahydrofuran-2-yl)methyl]-phosphoric acid diester Following essentially the procedure of Example (1g), and using in place of the compound prepared in (1f), an approximately equivalent amount of the compound prepared in (a) above, the desired compound was obtained.

Preparation of the title compound

Following essentially the last step of the procedure in preparing the compound of Example 1, and using in place of the compound prepared in (1g), an approximately equivalent amount of the compound prepared in (b) above, a brown resin was obtained as the crude product. The crude product was then dissolved in a mixture of tetrahydrofuran and water in a ratio of 19:1 and the resultant solution was then passed through a column of Amberlite MB-3 ion-exchange resin. The eluate was then evaporated in vacuo and chromatographed in essentially the manner described above in Example 1 to obtain a product which was precipitated from methylene chloride with acetone to yield the title compound as a creamy-white solid, m.p. 170°–175° C. (dec.).
PAIA test—IC$_{50}$—3.5 μM
TEST A—IC$_{50}$—0.47 μM TEST C—ED$_{50}$—0.3 mg/kg (ia)
TEST D—ED$_{50}$—1.5 mg/kg (iv)

EXAMPLE 4

3-[2-[(2-Octadecylaminocarbonyloxymethyl tetrahydrofuran-2-yl-methoxy)-hydroxyphosphinyloxy]-ethane]-thiazolium hydroxide-4-oxide, bromide salt

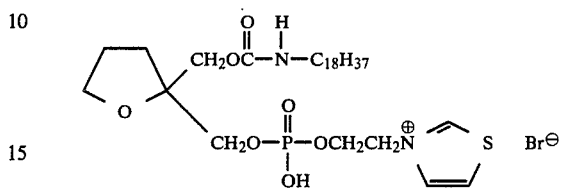

Following essentially the last step of the procedure in preparing the compound of Example 1, but omitting the use of silver carbonate, and using in place of the compound prepared in (1g), an approximately equivalent amount of the compound of Example (3b), the title compound was obtained as a tan-colored solid, m.p. 185°–190° C. (dec.)

EXAMPLE 5

2-[Hydroxy(tetrahydro)-2-(octadecyl-5-oxo-2-furanyl)-methoxyphosphinyloxy]-ethane thiazolium hydroxide-inner salt-4-oxide

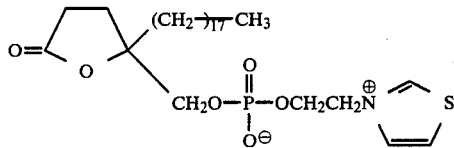

(a) Preparation of 1-benzyloxy-2-eicosanol

Following essentially the procedure of Example (1a), and using in place of octadecyl-3-butenyl ether, an approximately equivalent amount of 1-epoxyeicosane, a waxy solid was obtained.

(b) Preparation of 1-benzyloxy-2-eicosanone

Following essentially the procedure of Example (1b), and using in place of the compound prepared in (1a), an approximately equivalent amount of the compound prepared in (a) above, a white solid was obtained.

(c) Preparation of 5-benzyloxymethyl-5-hydroxy-1-tricosene

Following essentially the procedure of Example (1c) and using in place of the compound prepared in (1b), an approximately equivalent amount of the compound prepared in (b) above, a colorless oil was obtained.

(d) Preparation of 5-benzyloxymethyl-2-hydroxy-5-octadecyl tetrahydrofuran

Following essentially the procedure of Example (1d), and using in place of the compound prepared in (1c), an approximately equivalent amount of the compound prepared in (c) above, a colorless oil was obtained.

(e) Preparation of 5-benzyloxymethyl-5-octadecyl-4,5-dihydro-2(3H)-furanone

Following essentially the procedure of Example (1e), and using in place of the compound prepared in (1d), an approximately equivalent amount of the compound prepared in (d) above, a colorless oil was obtained.

(f) Preparation of 5-hydroxymethyl-5-octadecyl-4,5-dihydro-2-(3H)-furanone

Following essentially the procedure of Example (1f), and using in place of the compound prepared in (1e), an approximately equivalent amount of the compound prepared in (e) above, a white solid was obtained.

(g) Preparation of 2-bromoethyl-[(2-octadecyl(tetrahydro)-5-oxofuran-2-yl)methyl]-phosphoric acid diester Following essentially the procedure of Example (1g), and using in place of the compound prepared in (1f), an approximately equivalent amount of the compound prepared in (f) above, a white solid was obtained.

Preparation of the title compound

Following essentially the last step of the procedure in preparing the compound of Example 1, and using in place of the compound prepared in (1g), an approximately equivalent amount of the compound prepared in (g) above, a white solid was obtained, m.p. >122° C. (dec.)

EXAMPLE 6

2-[Hydroxy(tetrahydro)-2-(octadecyl-2-furanyl)-methoxyphosphinyloxy]-ethane thiazolium hydroxide-inner salt-4-oxide

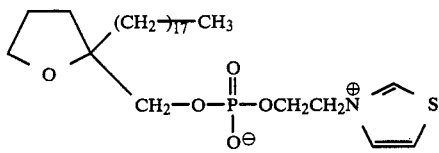

(a) Preparation of 2-benzyloxymethyl-2-octadecyl-tetrahydrofuran 11.5 g (26 mmol) of the compound prepared in 5d) above was dissolved in 120 ml of dichloromethane containing 4.54 g (39 mmol) of triethylsilane and the reaction mixture was cooled under a nitrogen atmosphere to −20° C. To the cooled mixture was added 4.26 g (30 mmol) of boron trifluoride etherate and, after 1 hour, a saturated aqueous sodium bicarbonate solution was added. The resultant mixture was then warmed to room temperature and after being submitted to extractive isolation, chromatography on silica gel yielded a colorless oil.

(b) Preparation of 2-hydroxymethyl-2-octadecyl-tetrahydrofuran

Following essentially the procedure of Example (1f), and using in place of the compound prepared in (1e), an approximately equivalent amount of the compound prepared in (a) above, a white solid was obtained.

(c) Preparation of 2-bromoethyl-[(2-octadecyl-tetrahydrofuran-2-yl)-methyl]-phosphoric acid diester Following essentially the procedure of Example (1g), and using in place of the compound prepared in (1f), an approximately equivalent amount of the compound prepared in (b) above, a white solid was obtained.

Preparation of the title compound

Following essentially the last step of the procedure in preparing the compound of Example 1, and using in place of the compound prepared in (1g), an approximately equivalent amount of the compound prepared in (c) above, a white solid was obtained, m.p. 198°-204° C. (dec.)

EXAMPLE 7

3-[2-[(2-octadecylaminocarbonyloxymethyl-tetrahydrofuran-2-yl-methoxy)-hydroxyphosphinyloxy]-ethane]-quinolinium hydroxide-inner salt-4-oxide

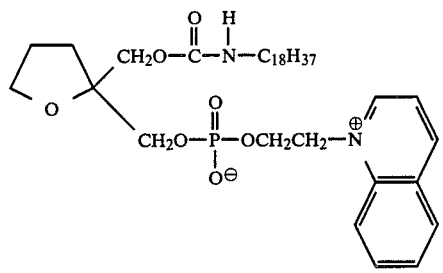

Following essentially the last step of the procedure in preparing the compound of Example 1, and using in place of the compound prepared in (1g), an approximately equivalent amount of the compound prepared in (3b), and in place of the thiazole, an approximately equivalent amount of quinoline, the title compound was obtained as a solid, m.p. >105° C. (dec.)

EXAMPLE 8

3-[6-[(2-Octadecylaminocarbonyloxymethyl-tetrahydrofuran-2-yl-methoxy)-hydroxyphosphinyloxy]-hexane]-thiazolium hydroxide-inner salt-8-oxide

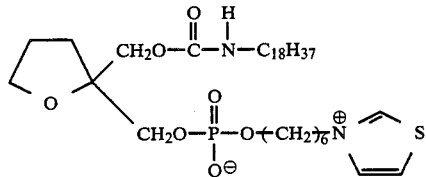

(a) Preparation of 6-bromohexyl-[(2-octadecylaminocarbonyloxymethyl-tetrahydrofuran-2-yl)-methyl]-phosphoric acid diester Following essentially the procedure of Example (1g), and using in place of the compound prepared in (1f), an approximately equivalent amount of the compound prepared in (3a), and in place of the 2-bromoethylphosphorodichloridate, an approximately equivalent amount of 6-bromohexylphosphorodichloridate, a white solid was obtained.

Preparation of the title compound

Following essentially the last step of the procedure in preparing the compound of Example 1, and using in plate of the compound prepared in (1g), an approximately equivalent amount of the compound prepared in (a) above, the title compound was obtained as a solid, m.p. 65°–70° C. (dec.)

EXAMPLE 9

3-[2-[(2-(9-Octadecenyl)aminocarbonyloxymethyl-tetrahydrofuran-2-yl-methoxy)-hydroxyphosphinyloxy]-ethane]-thiazolium hydroxide-inner salt-4-oxide

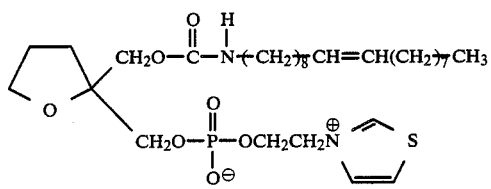

(a) Preparation of 2-hydroxymethyl-2-(9-octadecenyl)aminocarbonyloxy tetrahydrofuran Following essentially the procedure of Example (3a), and using in place of n-octadecylisocyanate, an equivalent amount of n-octadec-9-enylisocyanate, a white solid was obtained.

(b) Preparation of 2-bromoethyl-[(2-(9-octadecenyl)aminocarbonyloxymethyl-tetrahydrofuran-2-yl)-methyl]-phosphoric acid diester Following essentially the procedure of Example (1g), and using in place of the compound prepared in (1f), an approximately equivalent amount of the compound prepared in (a) above, a white solid was obtained.

Preparation of the title compound

Following essentially the last step of the procedure in preparing the compound of Example 1, and using in place of the compound prepared in (1g), an approximately equivalent amount of the compound prepared in (b) above, the title compound was obtained as a waxy solid.

What is claimed is:
1. A compound of formula I:

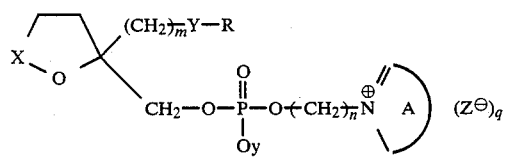

where
R is n-$C_{12}$-$C_{20}$ alkyl, alkenyl or alkynyl; or $C_{12}$-$C_{24}$ alkoxyalkyl;
X is $CH_2$ or C=O;
Y is $CH_2$; O;

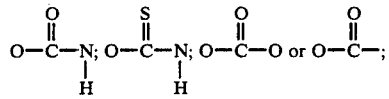

A, together with the nitrogen atom, forms an unsubstituted 5- or 6-membered, monocyclic ring which may optionally contain one further hetero atom selected from nitrogen and sulfur; a 5- or 6-membered, monocyclic ring which may optionally contain one further hetero atom selected from nitrogen and sulfur and which is either mono-, di- or trisubstituted by $C_1$-$C_4$ alkyl or monosubstituted by $CF_3$, halo, COOH or $COOCH_3$; an unsubstituted 10-membered, bicyclic ring which may optionally contain one further nitrogen atom; or a 10-membered, bicyclic ring which may optionally contain one further nitrogen atom and which is either mono-, di- or trisubstituted by $C_1$-$C_4$ alkyl or monosubstituted by $CF_3$, halo, COOH or $COOCH_3$;
$Z^\ominus$ is a pharmaceutically acceptable anion;
m is an integer 1 or 2;
n is an integer 2 to 8; and
y is $\ominus$ and q is O or y is H and q is 1.

2. A compound according to claim 1 of formula Ia:

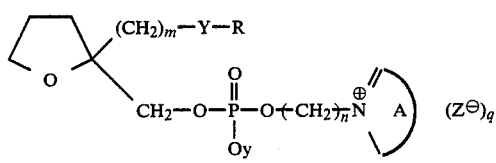

where R, Y, A, $Z^\ominus$, m, n, y and q are as defined in claim 1.

3. A compound according to claim 2 of formula Ia':

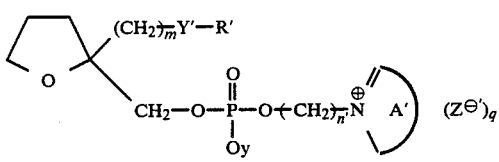

where
R' is n-$C_{14}$-$C_{20}$ alkyl, alkenyl or alkynyl; or $C_{12}$-$C_{20}$ alkoxyalkyl;
Y' is $CH_2$; O;

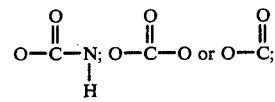

A', together with the nitrogen atom, forms an substituted thiazolium, pyridinium, pyridazinium, quinolinium or isoquinolinium ring, or a thiazolium, pyridinium, pyridazinium, quinolinium or isoquinolinium ring which is either mono-, di- or trisubstituted by $C_1$-$C_4$-alkyl or monosubstituted by $CF_3$, halo, COOH or $COOCH_3$;
$Z^{\ominus'}$ is chloride; bromide; iodide; phenylsulfonate; toluenesulfonate; $C_1$-$C_4$-alkylsulfonate, carboxylate or tetrafluoroborate;
n' is an integer 2 to 6;
and m, y and q are as defined in claim 2.

4. A compound according to claim 3 of formula Ia'':

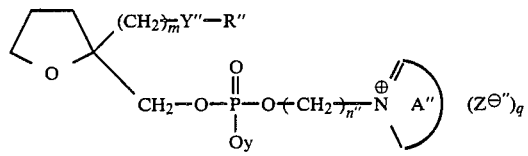

where
R'' is n-$C_{16}$-$C_{20}$ alkyl, alkenyl or alkynyl; or $C_{14}$-$C_{18}$ alkoxyalkyl;
Y'' is O;

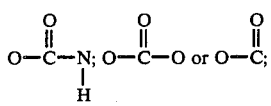

A'', together with the nitrogen atom, forms an unsubstituted thiazolium, pyridinium or quinolinium ring, or a thiazolium, pyridinium or quinolinium ring which is either mono-, di- or trisubstituted by $C_1$-$C_4$ alkyl or monosubstituted by $CF_3$, halo, COOH or $COOCH_3$;
$Z^{\ominus''}$ is chloride; bromide; $C_1$-$C_4$ alkylsulfonate or carboxylate;
n'' is an integer 2 to 4;
and m, y and q are as defined in claim 3.

5. A compound according to claim 4 of formula Ia''':

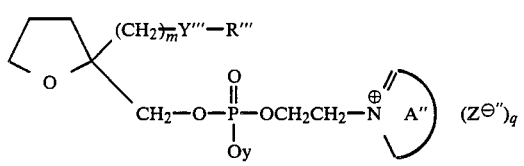

where
R''' is n-$C_{16}$-$C_{18}$ alkyl, alkenyl or alkynyl; or $C_{14}$-$C_{18}$-alkoxyalkyl;
Y''' is a O;

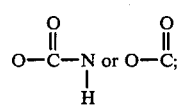

and A'', $Z^{\ominus''}$, m, y and q are as defined in claim 4.

6. A compound according to claim 5 having the formula

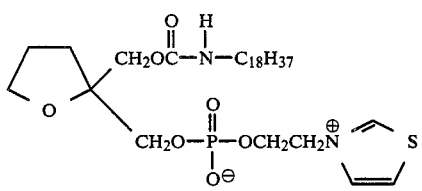

7. A compound according to claim 1 of formula Ib:

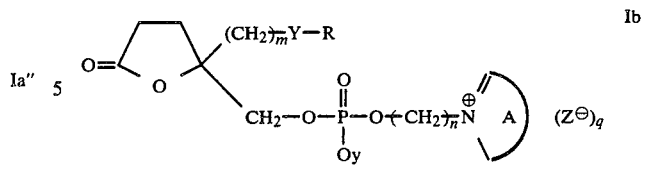

where R, Y, A, $Z^{\ominus}$, m, n, y and q are as defined in claim 1.

8. A compound according to claim 7 of formula Ib':

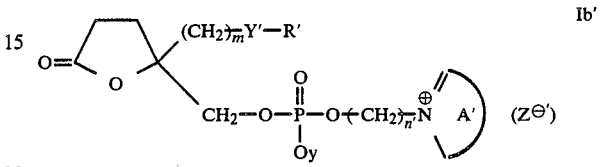

where
R' is n-$C_{14}$-$C_{20}$ alkyl, alkenyl or alkynyl; or $C_{12}$-$C_{20}$ alkoxyalkyl;
Y' is $CH_2$; O;

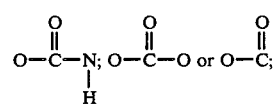

A', together with the nitrogen atom, forms an unsubstituted thiazolium, pyridinium, pyridazinium, quinolinium or isoquinolinium ring, or a thiazolium, pyridinium, pyridazinium, quinolinium or isoquinolinium ring which is either mono-, di- or trisubstituted by $C_1$-$C_4$-alkyl or monosubstituted by $CF_3$, halo, COOH or $COOCH_3$;
$Z^{\ominus'}$ is chloride; bromide; iodide; phenylsulfonate; toluenesulfonate; $C_1$-$C_4$-alkylsulfonate; carboxylate or tetrafluoroborate;
n' is an integer 2 to 6;
and m, y and q are as defined in claim 7.

9. A compound according to claim 8 of formula Ib'':

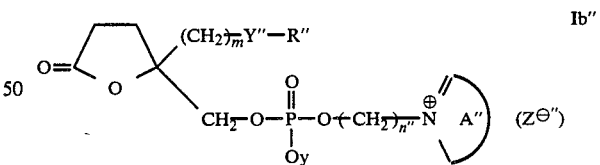

where
R'' is n-$C_{16}$-$C_{20}$ alkyl, alkenyl or alkynyl; or $C_{14}$-$C_{18}$ alkoxyalkyl;
Y'' is O;

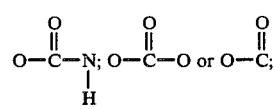

A'', together with the nitrogen atom, forms an unsubstituted thiazolium, pyridinium or quinolinium ring, or a thiazolium, pyridinium or quinolinium ring which is either mono-, di- or trisubstituted by $C_1$–$C_4$ alkyl or monosubstituted by $CF_3$, halo, COOH or $COOCH_3$;

$Z^\ominus{''}$ is chloride; bromide; $C_1$–$C_4$ alkylsulfonate or carboxylate;

n'' is an integer 2 to 4;

and m, y and q are as defined in claim 8.

10. A compound according to claim 9 of formula Ib''':

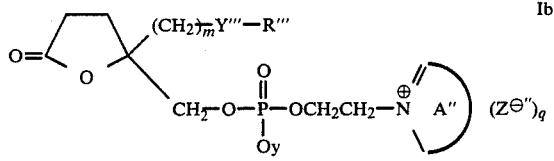

where

R''' is n-$C_{16}$–$C_{18}$ alkyl, alkenyl or alkynyl; or $C_{14}$–$C_{18}$-alkoxyalkyl;

Y''' is O;

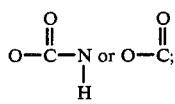

and A'', $Z^\ominus{''}$, m, y and q are as defined in claim 9.

11. A compound according to claim 10 having the formula:

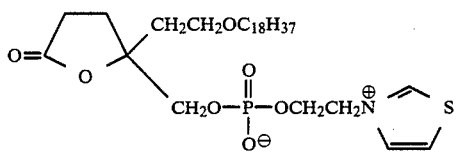

12. A method of inhibiting PAF-induced blood platelet aggregation comprising administering to a subject afflicted therewith a therapeutically effective amount of a compound according to claim 1.

13. A method according to claim 12 comprising administering a therapeutically effective amount of the compound of the formula

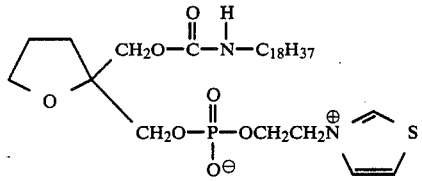

14. A method according to claim 12 comprising administering a therapeutically effective amount of the compound of the formula

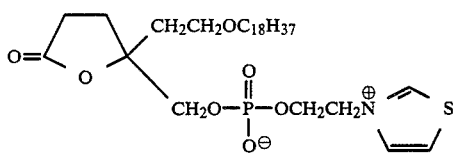

15. A method of inhibiting PAF-mediated bronchoconstriction and extravasation comprising administering to a subject afflicted therewith a therapeutically effective amount of a compound according to claim 1.

16. A method according to claim 15 comprising administering a therapeutically effective amount of the compound of the formula

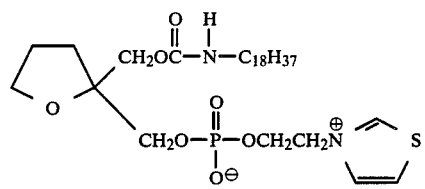

17. A method according to claim 15 comprising administering a therapeutically effective amount of the compound of the formula

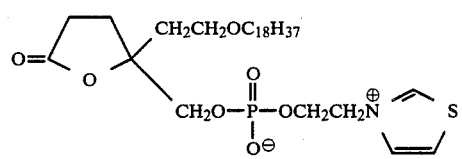

18. A method of inhibiting PAF-induced hypotension comprising administering to a subject afflicted therewith a therapeutically effective amount of a compound according to claim 1.

19. A method according to claim 18 comprising administering a therapeutically effective amount of the compound of the formula

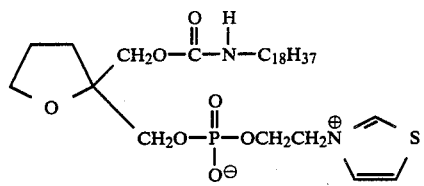

20. A method according to claim 18 comprising administering a therapeutically effective amount of the compound of the formula

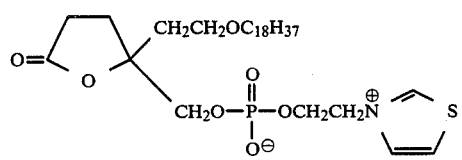

21. A method of inhibiting PAF-induced ischemic bowel disease comprising administering to a subject afflicted therewith a therapeutically effective amount of a compound according to claim 1.

22. A method according to claim 21 comprising administering a therapeutically effective amount of the compound of the formula 23. A method according to claim 21 comprising administering a therapeutically effective amount of the compound of the formula

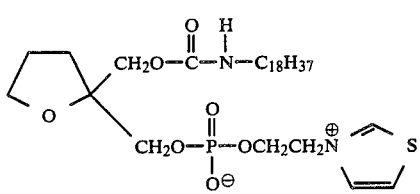

24. A pharmaceutical composition useful in inhibiting PAF-induced blood platelet aggregation, PAF-mediated bronchoconstriction and extravasation, PAF-induced hypotension and PAF-induced ischemic bowel disease comprising a pharmaceutically acceptable carrier and a therapeutically effective amount of a compound according to claim 1.

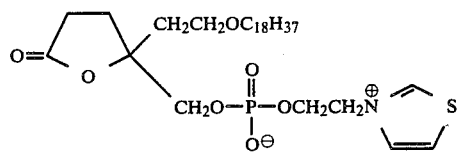

* * * * *